United States Patent
Townsend et al.

(10) Patent No.: US 6,472,167 B1
(45) Date of Patent: *Oct. 29, 2002

(54) METHOD AND COMPOSITION FOR DETECTING BACTERIAL CONTAMINATION IN FOOD PRODUCTS

(75) Inventors: David E. Townsend, Scarborough; Chun-ming Chen, Falmouth, both of ME (US)

(73) Assignee: BioControl Systems, Inc., Bellevue, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/038,665

(22) Filed: Feb. 24, 1998

Related U.S. Application Data

(63) Continuation of application No. 08/484,593, filed on Jun. 7, 1995, now Pat. No. 6,387,650.

(51) Int. Cl.⁷ .................................................. C12Q 1/04
(52) U.S. Cl. ............................. 435/34; 435/19; 435/24; 435/39
(58) Field of Search ............................ 435/34, 18, 19, 435/24, 29, 30, 38, 39, 243, 968; 436/172

(56) References Cited

U.S. PATENT DOCUMENTS

| | | | |
|---|---|---|---|
| 3,206,317 A | | 9/1965 | Golber |
| 3,496,066 A | | 2/1970 | Berger et al. |
| 4,129,483 A | | 12/1978 | Bochner ..................... 195/100 |
| 4,235,964 A | | 11/1980 | Bochner |
| 4,591,554 A | * | 5/1986 | Koumura et al. .............. 435/18 |
| 4,925,789 A | | 5/1990 | Edberg |
| 5,064,756 A | * | 11/1991 | Carr et al. ..................... 435/32 |
| 5,236,827 A | * | 8/1993 | Sussman et al. ............... 435/34 |
| 5,364,767 A | | 11/1994 | Flowers et al. |
| 5,443,987 A | | 8/1995 | DeCicco et al. |
| 5,464,755 A | * | 11/1995 | Bochner ....................... 435/34 |
| 5,726,031 A | * | 3/1998 | Roth et al. ..................... 435/34 |
| 5,726,062 A | | 3/1998 | Numa et al. .................. 436/86 |
| 6,387,650 B1 | * | 5/2002 | Townsend et al. ............. 435/34 |

FOREIGN PATENT DOCUMENTS

| | | |
|---|---|---|
| EP | 0 122 028 A1 | 10/1984 |
| EP | 0254771 | 2/1988 |
| FR | 2728587 | 6/1996 |
| WO | 95/04157 | 2/1995 |

OTHER PUBLICATIONS

*Compendium of Methods for the Microbiological Examination of Foods*, Third Edition, Edited by Carl Vanderzant and Don F. Splittstoesser, Compiled by the APHA Technical Committee on Microbiological Methods for Foods (Copy not provided).

\* cited by examiner

*Primary Examiner*—Ralph Gitomer
(74) *Attorney, Agent, or Firm*—Seed Intellectual Property Law Group PLLC

(57) ABSTRACT

This invention relates to a method for detecting the existence or measuring the concentration of total viable bacteria in a test sample from a food product. A medium is provided which contains three or more different enzyme substrates each having a nutrient moiety and a detectable moiety linked together. When a substrate is hydrolysed by a bacterial enzyme to create a separate detectable moiety, it causes or produces a detectable signal. These substrates produce detectable signals when any one of a phosphatase enzyme, a glycosidase enzyme or a peptidase enzyme is present in the medium.

17 Claims, No Drawings

METHOD AND COMPOSITION FOR DETECTING BACTERIAL CONTAMINATION IN FOOD PRODUCTS

This is a continuation of application Ser. No. 08/484,593 filed Jun. 7, 1995, now U.S. Pat. No. 6,387,650.

FIELD OF THE INVENTION

This invention relates to methods and compositions for detecting the existence or measuring the concentration of bacterial contamination in food products.

BACKGROUND OF THE INVENTION

Ground beef and chicken are susceptible to rapid spoilage by psychotropic bacteria which thrive at refrigeration temperatures. As a result, these products have very short shelf-lives which are directly related to the initial concentration of contaminating bacteria.

Current methods for measuring the concentrations of bacterial contamination in ground beef and chicken include the standard plate count (Difco Laboratories) as well as the Petri Film system (3M) (see generally, *Compendium of Methods for the Microbiological Examination of Foods*, Third Edition, Edited by Carl Vanderzant and Don F. Splittstoesser, Compiled by the APHA Technical Committee on Microbiological Methods for Foods). These methods require around 48 hours of incubation in a 35° C. incubator before the results can be read. Both methods utilize a solid nutrient base to support the growth of individual cells into bacterial colonies. Many food-borne bacteria are incapable of growing into colonies on these surfaces when incubated at 35° C.; thus, the concentrations of total viable bacteria measured by the above methods may be underestimated.

In addition, the long incubation periods of these methods can cause these food products to remain in storage for several days until the concentrations of contaminating bacteria are known. If these tests could be completed in a shorter period of time it would allow companies to release their products sooner so as to lower costs, increase sales, and provide better product to the consumer.

There have been attempts to measure the bacterial concentration in food by measuring specific metabolic by-products of individual microorganisms. These methods include: electrical impedance assays, ATP assays, antibody-based assays, and carbon-14 labelled substrate assays. Indicators of microbial growth have also been used to monitor the growth of target microbes which change color only after growth of the target microbe is detected. These indicators normally react chemically with a metabolic by-product produced by the is target microbes resulting in a.color change in the medium. Examples of chemicals which change color in the presence of pH changes associated with growth include phenol red, bromocresol blue, and neutral red. For example, Golber, U.S. Pat. No. 3,206,317, uses phenol red, a chemical which changes color in the presence of acidic waste products produced by the target microbe. Berger et al., U.S. Pat. No. 3,496,066, describes the use of compounds which bacteria convert to dyestuffs, e.g., tropinones and dioxanes, Bochner, U.S. Pat. No. 4,129,483 describes using a non-biodegradable substance (tetrazolium) which is chemically reduced to produce a color change. In all of these examples, the indicator is a compound which does not serve as a source of a required nutrient.

Edberg (U.S. Pat. No. 4,925,789), incorporated by reference herein, describes a selective growth medium for a microbe containing a nutrient indicator which can only be metabolized by a target microbe. When metabolized by a target microbe, the nutrient indicator releases a moiety which imparts a detectable change to the medium.

SUMMARY OF THE INVENTION

The present invention relates to a bacterial growth medium and methods for detecting the existence or measuring the concentration of bacteria in a test sample. The claimed medium and methods measure viable bacteria as a function of the activities of several classes of bacterial enzymes, including, but not limited to, phosphatases, glycosidases (such as glucosidases), and aminopeptidases. The presence of at least one of these groups of enzymes in any given bacterial species will be detected by the appearance of a detectable signal such as a fluorescent signal. Therefore, this invention is useful in detecting the existence or measuring the concentration of total viable bacteria or at least a multitude of viable bacteria in a test sample in a single assay. In specific examples, cocktails of enzyme substrates are made to measure the concentration of bacterial contamination in food products, such as ground beef and chicken.

Thus, in one aspect, the invention features a bacterial growth medium containing three or more different enzyme substrates each hydrolysed by a different bacterial enzyme to cause or produce a detectable signal.

In a preferred embodiment, the three or more different enzyme substrates each has both a nutrient moiety and a detectable moiety linked together by a covalent bond. Each of these enzyme substrates is hydrolysed by a different bacterial enzyme to produce a separate detectable moiety which causes or produces a detectable signal in the medium. In a further preferred embodiment, the detectable signals caused or produced are of identical type.

By "medium" is meant a solid, powder or liquid mixture which contains all or substantially all of the nutrients necessary to support bacterial growth. Amino acids, minerals, vitamins and other elements known to those skilled in the art to be necessary for bacterial growth are provided in the medium, including, but not limited to, those disclosed in U.S. application Ser. Nos. 08/334,788 (abandoned in favor of C-I-P application 08/423,134 filed Apr. 18, 1995 and issued as U.S. Pat. No. 5,610,029 on Mar. 11, 1997), and Ser. No. 08/335,149, (issued as a U.S. Pat. No. 5,620,865 on Apr. 15, 1997), both filed on Nov. 4, 1994, incorporated by reference herein. In a preferred embodiment, the medium is liquid.

For example, the following components are provided in the medium in approximately the amounts indicated. Those in the art will understand that not every component is required. Components may also be substituted with other components of similar properties. The amounts of components may also be varied.

Amino acids may be provided from a variety of sources. These can be provided from natural sources (e.g., extracts of organisms), as mixtures, or in purified form. The natural mixtures may contain varying amounts of such amino acids and vitamins. Not all amino acids must be provided, and the relative amount of each can vary. For general guidance, specific amounts of such amino acids and vitamins are indicated below. These amounts are for guidance only and are not limiting in this invention. Those in the art will recognize that many different combinations of amino acids and vitamins can be used in the medium of this invention. The lists provided below exemplify just one such example. Normally, only amino acids which cannot be synthesized endogenously by the microorganisms to be detected must be provided. However, other amino acids may be provided without departing from the medium of the invention.

The medium preferably includes at least the following amino acids in approximately the following amounts (per liter of medium): Alanine (0.015 to 0.60 grams), Arginine (0.080 to 3.2 grams), Aspartic Acid (0.018 to 0.72 grams), Cystine (0.09 to 3.6 grams), Glutamic Acid (0.030 to 1.20 grams), Glycine (0.050 to 2.00 grams), Histidine (0.025 to 1.00 grams), Isoleucine (0.035 to 1.40 grams), Leucine (0.040 to 1.60 grams), Lysine (0.050 to 2.00 grams), Methionine (0.01 to 0.50 grams), Phenylalanine (0.01 to 0.90 grams), Proline (0.02 to 2.80 grams), Serine (0.01 to 0.40 grams), Threonine (0.01 to 1.10 grams), Tryptophan (0.002 to 0.26 grams), Tyrosine (0.01 to 1.20 grams), and Valine (0.02 to 1.10 grams).

Salts may be provided as a source of ions upon dissociation. Such salts may include (per liter of medium): potassium chloride (e.g., about 0.5 to 1.5 grams); copper sulfate (e.g., about 40 to 50 $\mu$g); ammonium acetate or ammonium sulfate (e.g., about 4.0 to 6.0 grams); potassium iodide (e.g., about 50.0 to 150.0 $\mu$g); ferric chloride (e.g., about 150.0 to 250.0 $\mu$g); manganese sulfate (e.g., about 300.0 to 500.0 $\mu$g); sodium molybdate (e.g., about 150.0 to 250.0 $\mu$g); zinc sulfate (e.g. about 300.0 to 500.0 $\mu$g); and sodium chloride (e.g. about 0.05 to 0.15 g).

Other inorganic moieties may be included to aid microbial growth. These include the following (to the extent not already provided in the above sources of various chemical entities and described in amounts per liter): Phosphorus (about 0.5 mg), Potassium (about 0.4 mg), Sodium (about 30 to 60 mg), and trace amounts of Calcium, Magnesium, Aluminum, Barium Chloride, Cobalt, Copper, Iron, Lead, Manganese, Sulfur, Tin and Zinc.

Vitamins required for growth and reproduction of the microorganism sought to be detected may also be provided. These can be provided in a pure form or as part of a more complex medium. Such vitamins may be present in approximately the following amounts (per liter of medium): Biotin (about 0.15 to 60 $\mu$g), Pantothenic Acid (about 15.0 to 65.0 $\mu$g), Pyridoxine (about 2.0 to 9.0 $\mu$g), Riboflavin (about 10.0 to 50.0 $\mu$g), Folic acid (about 5.00 to 50.00 $\mu$g), Thiamine (about 10.0 to 50.0 $\mu$g), Vitamin B12 (about 0.20 to 0.50 $\mu$g), and Niacin (about 15.0 to 55.0 $\mu$g).

By "bacterial enzyme" is meant an enzyme whose enzymatic activity such as the ability to hydrolyse a substrate or a plurality of substrates is characteristic of a bacterium or a plurality of bacteria. In this invention, the enzymatic activities of a bacterial enzyme or bacterial enzymes are used to detect or measure the concentration of bacteria in a test sample. The bacterial enzymes include all those known to one skilled in the art, including, but not limited to, those listed in *Enzymes,* 3rd edition, edited by Malcolm Dixson, Edwin C. Webb, C. J. R. Thorne, and K. F. Tipton, 1979, Academic Press, U.S.A. In a preferred embodiment, the bacterial enzyme is selected from the group consisting of alkaline phosphatase, acid phosphatase, esterase, lipase, N-acetyl-β-D-galactosaminidase, N-acetyl-β-D-glucosaminidase, Neuraminidase, L-arabinopyranosidase, β-D-fucosidase, α-L-fucosidase, β-L-fucosidase, α-D-galactosidase, β-D-galactosidase, α-D-glucosidase, β-D-glucosidase, β-D-glucuronidase, α-D-mannosidase, pyrophosphatase, sulfatase, β-D-xylosidase, peptidase (preferably an aminopeptidase, more preferably an (L or D amino acid)—aminopeptidase), trypsin, chymotrypsin, and phosphohydrolase.

By "substrate." is meant a molecule or substance on which a bacterial enzyme acts. The enzymatic reaction usually involves hydrolysing one or more covalent bonds, forming one or more covalent bonds, or both. A covalent bond in the substrate between the nutrient moiety and the detectable moiety is hydrolysed by a bacterial enzyme to produce a separate detectable moiety. The substrates include all those known to one skilled in the art, including, but not limited to, those in the product listing of AerChem, Inc. with detectable moieties attached thereto (see Table I).

By "nutrient moiety" is meant a molecule or substance which is a nutrient or metabolic source for a bacterium, including, but not limited to, vitamins, minerals (e.g., phosphorus in the form of phosphate), trace elements, amino acids (e.g., L-alanine), carbon (e.g., glucose), or nitrogen.

By "detectable signal" is meant a characteristic change in a medium or sample that is observable or measurable by physical, chemical, or biological means known to those skilled in the art. Such a detectable signal may be a change in emission or absorbance of visible or invisible light or radio waves at a certain wavelength, electrical conductivity, hybridization, enzymatic reaction, emission of gas, or odor. A detectable signal may also be a change in physical state such as between solid, liquid and gas. In preferred embodiments, detectable signals include a change in color or fluorescent emission of the medium.

By "identical type of detectable signal" is meant that the separate detectable moieties hydrolysed from different enzyme substrates cause or produce detectable signals that are measurable by the same or substantially the same physical, chemical or biological parameter, including, but not limited to, color, fluorescent emission, odor, enzymatic reaction, hybridization, or electric conductivity (although the intensity or quantity of signals caused or produced by different separate detectable moieties may be different). For example, yellow colors of different intensity would be considered of the identical type. Color change and fluorescence would not be considered to be identical type of detectable signal.

By "detectable moiety" is meant a molecule or substance which can be covalently linked to a nutrient moiety or exists as a separate entity by itself. The detectable moiety does not cause or produce a detectable signal when it is covalently bonded to a nutrient moiety. However, when an enzyme from a bacterium hydrolyses the substrate, a detectable moiety is released and causes or produces a detectable signal. In preferred embodiments, the detectable moieties are chromogens which produce a color change observable in the visible wavelength range or fluoresces when properly excited by an external energy source. Examples of detectable moieties include, but are not limited to, orthonitrophenyl, phenolphthalein, and 4-methylumbelliferone moieties.

The invention also features a method of using the medium to detect the existence or measure the concentration of bacterial contamination in a test sample. The medium is inoculated with the test sample and incubated under a condition suitable for bacterial growth for a certain time period (preferably no more than 24 hours, more preferably no more than 15 hrs, even more preferably no more than 10 hours). Then the detectable signal is measured as an indication of the concentration of bacteria in the test sample. Using this method, a detectable signal is produced when at least one of the three or more different bacterial enzymes is or are present in the bacteria which are incubating in the medium.

By "test sample" is meant a piece, fraction, aliquot, droplet, portion, fragment, volume, or tidbit taken from a food product such as ground beef or chicken, a human or animal test subject, a soil, water, air or other environmental source, or any other source whose bacterial concentration is to be measured. A test sample may be taken from a source using techniques known to one skilled in the art, including, but not limited to, those described or referred to in *Compendium of Methods for the Microbiological Examination of Foods,* Third Edition, Edited by Carl Vanderzant and Don F. Splittstoesser, Compiled by the APHA Technical Committee on Microbiological Methods for Foods, incorporated by reference herein.

By "bacteria" is meant one or more viable bacteria existing or co-existing collectively in a test sample. The term may refer to a single bacterium (e.g., *Aeromonas hydrophilia, Aeromonas caviae, Aeromonas sobria, Streptococcus uberis, Enterococcus faecium, Enterococcus faecalis, Bacillus sphaericus, Pseudomonas fluorescens, Pseudomonas putida, Serratia liquefaciens, Lactococcus lactis, Xanthomonas maltophilia, Staphylococcus simulans, Staphylococcus hominis, Streptococcus constellatus, Streptococcus anginosus, Escherichia coli, Staphylococcus aureus, Mycobacterium fortuitum,* and *Klebsiella pneumonia*), a genus of bacteria (e.g., streptococci, pseudomonas and enterococci), a number of related species of bacteria (e.g., coliforms), an even larger group of bacteria having a common characteristic (e.g., all gram-negative bacteria), a group of bacteria commonly found in a food product, an animal or human subject, or an environmental source, or a combination of two or more bacteria listed above. The bacteria include those described or referred to in *Bergey's Manual of Systematic Bacteriology,* 1989, Williams and Wilkins, U.S.A., incorporated by reference herein.

In preferred embodiments, one of the substrates is hydrolysed by the enzyme alkaline phosphatase; another substrate is hydrolysed by the enzyme glycosidase, including, but not limited to, β-D-glucosidase; and a third substrate is hydrolysed by a peptidase (preferably an aminopeptidase, more preferably an (L or D amino acid)—aminopeptidase), including, but not limited to, L-alanine aminopeptidase; the detectable moiety is a fluorescent moiety such that when the detectable moiety is hydrolysed from a substrate, it causes or produces a fluorescent signal; the medium contains at least the following three substrates: 4-methylumbelliferyl phosphate, 4-methylumbelliferyl-β-D-glucoside and L-alanine-7-amido-4-methyl coumarin; and the medium is inoculated with a test sample from a food product, including, but not limited to, ground beef, chicken, milk, dairy products, and drinking water.

In another aspect, the invention features a bacterial growth medium containing two or more different enzyme substrates each hydrolysed by a different bacterial enzyme to cause or produce an identical type of detectable signal.

In a preferred embodiment, the two or more different substrates each has both a nutrient moiety and a detectable moiety linked together by a covalent bond. Each of these substrates is hydrolysed by a different bacterial enzyme to produce a separate detectable moiety which causes or produces an identical type of detectable signal.

The invention also features a method of using the medium to detect the existence or measure the concentration of bacteria in a test sample. The medium is inoculated with the test sample and incubated under a condition suitable for bacterial growth for a certain time period (preferably no more than 24 hours, more preferably no more than 15 hrs, even more preferably no more than 10 hours). Then the detectable signal is measured as an indication of the concentration of bacterial contamination in the test sample. Using this method, a detectable signal is produced when at least one of the two or more different bacterial enzymes is present in the incubation medium.

In preferred embodiments, the substrates are hydrolysed by an enzyme selected from the group consisting of alkaline phosphatase, glycosidase (which includes, but is not limited to, β-D-glucosidase), and peptidase (preferably an aminopeptidase, more preferably an (L or D amino acid)—aminopeptidase, including, but not limited to, L-alanine aminopeptidase); and the detectable moiety and the medium are analogous to those noted above.

In other embodiments, the invention uses the apparatus described by Naqui et al. in U.S. patent application Ser. No. 08/201,110, (issued as U.S. Pat. No. 5,518,892 on May 21, 1996) incorporated by reference herein, to quantify the concentration of bacterial contamination. An example of such an apparatus is sold by Idexx Laboratories Inc. under the name of Quanti Tray™. The quantifying step involves providing a test sample in a liquid form. The sample is placed or dispensed into the sample holding bag described by Naqui et al., and mixed with a medium to allow and promote growth of target bacteria within individual compartments. The mixture is incubated and the quantity and quality of the color or fluorescence change in each compartment is detected. The quantity and quality of positive compartment (i.e., a compartment having a detectable color or fluorescence change) is compared to a most probable number table which relates that value to the bacterial concentration of the test sample.

This invention has many advantages over the methods currently used to measure bacterial contamination. One advantage is its relatively short time to results. Certain psychotropic bacteria grow very slowly and can take from 48 to 72 hours before their colonies become large enough to count on an agar plate. However, countable colonies need not be present for the results of Applicant's test to be read. The fluorescent color produced by these bacteria in the invention appears much faster than their corresponding colonies which results in a much shorter detection time. Applicant's test can reduce the incubation period to 24 hours or less.

Another advantage of the invention has over standard methods is the absence of interference by bacterial overgrowth. This is a particular problem when Bacillus species are present because they tend to grow over other bacterial colonies in such a way that the plate is unreadable. The Bacillus species are common in food, particularly those that have been heat treated, such as pasteurized milk. This problem is avoided in the invention because it does not depend on counting individual bacterial colonies.

This invention can be used in microbiology laboratories involved in end product testing and/or quality control of food products, the meat and poultry industries, the dairy industry, and the water industry. The invention may be used to measure the concentration of total viable bacteria in drinking water.

This invention also relates to a growth medium and methods for detecting or measuring the concentration of yeasts, fungi, or other eukaryotic microorganisms in a test sample using a formulated medium and steps like those described above.

Other features and advantages of the invention will be apparent from the following description of the preferred embodiments, and from the claims.

DESCRIPTION OF THE PREFERRED EMBODIMENTS

In the following description, reference will be made to various methodologies known to those of skill in the chemical, biological and microbiological arts. Publications and other materials setting forth such known methodologies to which reference is made are incorporated herein by reference in their entireties as though set forth in full. The compositions, methods, and products of this invention are applicable to biological and environmental specimens, and are useful in the chemical, biological and microbiological arts for the detection of bacterial contamination.

Detecting Bacteria by Measuring Bacterial Enzyme Activities

Bacteria derive their nutrients from an array of sources. The ability to metabolize certain sources may be characteristic of a particular bacterium or group of bacteria. Families, groups or species of bacteria may share enzyme specificity for certain nutrients which are lacking in other bacteria. By taking advantage of the metabolic characteristics of bacteria, it is possible to test for the presence of these enzyme systems, and thus, the bacteria which display these enzyme systems themselves. See Edberg, supra. Many enzymes have been identified which are specific to particular groups of bacteria and o others likely will be identified in the future (see generally, *Bergey's Manual of Systematic Bacteriology*, 1989, Williams and Wilkins, U.S.A.).

For example, most gram negative bacteria, as a group, have L-alanine aminopeptidase enzyme activity. Substrates such as L-alanine-β-orthonitrophenyl, β-naphthalamide-β-L-alanine, α-naphthol-β-L-alanine, 4-methylumbelliferyl-β-L-alanine, and L-alanine-7-amido-4-methyl coumarin may be used in the medium to test for the presence of gram negative bacteria. The enzyme β-D-glucosidase is found in the Enterococcus group of bacteria. The enzyme may catalyze the hydrolysis of appropriate substrates containing chromogenic or fluorogenic moieties linked to a β-glucoside. This property may be used to indicate the presence or absence of enterococci in a sample. Substrates such as 4-methylumbelliferyl-β-D-glucopyranoside may be used to indicate the presence of enterococci. *Staphylococcus aureus* is capable of hydrolysing orthonitrophenyl phosphate. Thus, if the growth medium contains this substrate as a source of phosphate, *Staphylococcus aureus* will grow and a color change will be produced by the release of the orthonitrophenyl moiety. *Mycobacterium fortuitum* requires $SO_4$ as its source of sulfur, and this species can hydrolyse phenolphthalein-sulfate. Thus, in a selective medium whose only sulfur source is phenolphthalein-sulfate, this species will grow and produce a characteristic color change by release of the colored moiety. Furthermore, the enzyme β-D-glucuronidase is present in *E. coli*. Substrates such as orthonitrophenyl-β-D-glucuronide, β-naphthalamide-β-D-glucuronide, α-naphthol-β-D-glucuronide or methylumbelliferyl-β-D-glucuronide may be used in a medium for the detection of *E. coli*.

Substrates and Detectable Moieties

Substrates including a chromogenic moiety have been demonstrated to display a characteristic color change in samples containing target bacteria having a bacterial enzyme capable of hydrolysing the substrates. For example, in the presence of β-D-glucuronidase, orthonitrophenyl-β-D-glucuronide produces a color change to yellow, 4-methylumbelliferyl-β-D-glucuronide produces fluorescence after excitation at 366 nm, and bromo-chloro-indole-β-D-glucuronide produces a color change to blue when *E. coli* is present. In the presence of β-D-galactosidase, orthonitrophenyl-β-D-galactopyranoside produces a color change to yellow and 4-methylumbelliferyl-β-D-galactopyranoside produces fluorescence after excitation at 366 nm when *E. coli* is present.

Two substrates producing different types of detectable signals have been used for detecting the presence of *E. coli* among total coliform bacteria. 4-methylumbelliferyl-β-D-glucuronide may be used together with orthonitrophenyl-β-D-galactopyranoside. If any *E. coli* is present, the sample solution both changes color to yellow and emits fluorescence after excitation at 366 nm.

Table I is a list of substrates from AerChem, Inc. that may be used to detect bacterial enzyme activities.

A detectable moiety may be attached to a nutrient moiety by methods known to those skilled in the art. The methods generally feature coupling or conjugating a nutrient moiety to a detectable moiety, such as a chromogenic moiety. Examples of such methods are described by Edberg in U.S. Pat. No. 4,925,789, incorporated by reference herein.

The following non-limiting example features a liquid based bacterial growth medium used to quantify the total number of viable bacteria present in ground beef and chicken. This medium comprises 4-methylumbelliferyl phosphate (MUP), 4-methylumbelliferyl-β-D-glucoside (MUD), and L-alanine-7-amido-4-methyl coumarin (ala-AMC). An example of the composition is described in Table II. The composition of defined media is described in Table III. MUP, MUD, ala-AMC, and potassium nitrate were purchased from Sigma. Bacto Proteose Peptone No. 3 was purchased from DIFCO.

The substrate 4-methylumbelliferyl-β-D-glucoside is used to detect the presence of the enzyme β-D-glucosidase which is present in *Streptococci, Enterococci,* and other related bacteria commonly found in fresh meat.

The substrate L-alanine-7-amido-4-methylcoumarin is used to detect the presence of the enzyme L-alanine aminopeptidase which is found in most pseudomonas species and other gram negative bacteria. Applicant discovered that this substrate is particularly sensitive to the presence of psychotropic bacteria which cause spoilage in meat. Other substrates can be used in place of L-alanine-7-amido-4-methylcoumarin to detect other types of aminopeptidases in this group of bacteria without sacrificing sensitivity.

The substrate 4-methylumbelliferyl phosphate is used to detect the presence of phosphatases such as alkaline phosphatase and acid phosphatase which are found in most bacterial species. This enzyme substrate supports the detection of bacteria which lack or have diminished L-alanine aminopeptidase and β-D-glucosidase activities.

Because phosphatase, β-D-glucosidase, and L-alanine aminopeptidase are present in the vast majority of bacteria which contaminate ground beef and chicken, only one of these enzymes needs to be functional in the food-borne bacteria for viability to be detected. This test, therefore, has built-in redundant screens which support a highly accurate measure of total viable bacteria in ground beef and chicken.

The presence of bacteria is indicated by the appearance of a blue fluorescent color in the medium after it is exposed to an external ultra-violet lamp (366 nm wavelength). This test yields result after no more than 24 hours of incubation at 35° C.

The substrates MUP, MUD, or ala-AMC are hydrolysed by phosphatase, β-D-glucosidase, or L-alanine aminopeptidase to produce both nutrient and fluorescent moieties. The nutrient moieties (i.e., phosphate, glucose, and L-alanine) are consumed by the bacteria as a part of their normal metabolism. The fluorescent moieties (i.e., 4-methylumberiferone or 7-amino-4-methyl coumarin) produce fluorescent signals (maximum emission at 450 nm) which are used as indicators of bacterial viability.

The time required for the fluorescent color to appear is dependent upon the concentration of bacteria present in the reagent. Higher concentration of viable bacteria in the medium results in a proportional decrease in the time required for color development. Therefore, this test can be adapted to instrumentation because of the linear relationship between bacterial concentration and time to signal development, such as that described in Naqui et al., U.S. application Ser. No. 08/201,110, hereby incorporated by reference., Naqui et al. describes an accurate method for quantifying the number of bacteria in a liquid sample. The invention employs a novel apparatus for holding a liquid sample. The apparatus features a bag which is designed for receiving a liquid sample and subsequently distributes the liquid sample into separate compartments within the bag so that different aliquots of one or more sizes may be tested. The invention described in that application further allows quantifying the microorganisms present in the sample by adding a medium to promote growth of microorganisms, heat sealing the bag of the invention for about five seconds at a temperature of about 250° F. to 350° F., incubating the sample at an appropriate temperature for an appropriate length of time to allow growth of microorganisms, and recording and analyzing the results. The quantifying step involves detecting the quantity and quality of the color change in each compartment, and comparing that quantity and quality to a most probable number table which relates that value to the bacterial concentration of the test sample.

For example, each 10 ml Quanti Tray™ system contains 50 individual wells capable of holding 0.2 ml of medium. A 51st well is present which collects any "overfill" of medium not distributed into the first 50 wells. To begin the test the powder containing enzyme substrates is first dissolved in 10 ml of sterile water. Next, the reagent is inoculated with a predetermined volume of homogenized food material. Finally, the reagent is sealed in a 10 ml Quanti Tray™ and placed in a 35° C. incubator for 24 hours. The number of fluorescent wells present after incubation is compared against a most probable number (MPN) chart to determine the original concentration of bacteria present in the sample of food. Food containing higher than acceptable concentrations of contaminating bacteria can be retested to verify the results and/or disposed of to prevent distribution.

Because not all food is contaminated by the same bacteria found in ground beef and chicken, other enzyme targets may need to be selected to measure the total bacterial concentration of other types of food.

To design a medium for measuring the concentration of bacterial contamination in a test sample from another type of food or other sources prone to bacterial contamination, methods known to those skilled in the art (including, but not limited to, plating, nucleic acid hybridization study, microscopic observation, etc.) are used to identify bacteria species existing in the sample. Once the bacteria species are identified, one skilled in the art would be able to identify an enzyme or a group of enzymes that are characteristic of the bacteria species, and substrates acted on by the enzymes. Substrates having a nutrient moiety and a detectable moiety linked together by a covalent bond that is hydrolysed by the enzymes are produced to be used in the medium.

All publications referenced are incorporated by reference herein, including the nucleic acid sequences and amino acid sequences listed in each publication. All the compounds disclosed and referred to in the publications mentioned above are incorporated by reference herein, including those compounds disclosed and referred to in articles cited by the publications mentioned above.

Other embodiments of this invention are disclosed in the following claims.

TABLE I

4-MU-SUBSTRATES (4-Methylumbelliferyl-Substrates)

Bis(4-methylumbelliferyl)-phosphate
Bis(4-methylumbelliferyl)-phosphate Sodium salt
4-Methylumbelliferyl-acetate
4-Methylumbelliferyl-N-acetyl-β-D-galactosaminide
4-Methylumbelliferyl-N-aceteyl-β-D-glucosaminide
2'-(4-Methylumbelliferyl)-α-D-N-acetyl-neuraminic acid Sodium salt
4-Methylumbelliferyl-α-L-arabinopyranoside
4-Methylumbelliferyl-butyrate
4-Methylumbelliferyl-β-D-cellobiopyranoside
4-Methylumbelliferyl-β-D-cellotriose
4-Methylumbelliferyl-β-N,N'-diacetyl-chitobioside
4-Methylumbelliferyl-elaldate
4-Methylumbelliferyl-β-D-fucoside
4-Methylumbelliferyl-α-L-fucoside
4-Methylumbelliferyl-β-L-fucoside
4-Methylumbelliferyl-α-D-galactoside
4-Methylumbelliferyl-β-D-galactoside
4-Methylumbelliferyl-β-Dgalactoside-6-phosphate Ammonium salt
4-Methylumbelliferyl-α-D-gluoside
4-Methylumbelliferyl-β-D-gluoside
4-Methylumbelliferyl-β-D-glucuronide
4-Methylumbelliferyl-p-guanidinobenzoate hydrochloride
4-Methylumbelliferyl-heptanoate
4-Methylumbelliferyl-α-L-Iduronide
4-Methylumbelliferyl-laurate
4-Methylumbelliferyl-Ilgnocerate
4-Methylumbelliferyl-α-D-mannoside
4-Methylumbelliferyl-nonaoate
4-Methylumbelliferyl-oleate
4-Methylumbelliferyl-palmitate
4-Methylumbelliferyl-phosphate (free acid)
4-Methylumbelliferyl-phosphate Di(2-amino-2-methyl-1,3-propanediol) salt
4-Methylumbelliferyl-phosphate Dicyclohexylammonium salt
4-Methylumbelliferyl-phophate Disodium salt
4-Methylumbelliferyl-propionate
4-Methylumbelliferyl-pyrophosphate diester Disodium salt
4-Methylumbelliferyl-stearate
4-Methylumbelliferyl-sulfate Potassium salt
4-Methylumbelliferyl-6-sulfo-N-acetyl-β-D-glucosaminide
4-Methylumbelliferyl-β-D-N,N',N''-triacetylchitotriose
4-Methylumbelliferyl-4-trimethylammonium cinnamate chloride
4-Methylumbelliferyl-β-D-xylose AMC-SUBSTRATES (7-Amido-4-methycoumarin-Substrates)

N-α-Acetyl-lysine-7-amido-4-methycoumarin acetate
N-Acetyl-L-phenylalanyl-L-arginine-7-amido-4-methylcoumarin hydrochloride
L-Alanine-7-amido-4-methycoumarin
β-Alanine-7-amido-4-methylcoumarin TFA
D-Alanine-7-amido-4-methylcoumarin TFA
L-Alanine-4-amido-7-methylcoumarin TFA
L-Alanine-7-amido-4-methylcoumarin TFA
L-Alanine-7-amido-4-trifluoro-methylcoumarin TFA
L-Alanyl-L-alanyl-L-phenylalanine-7-amido-4-methylcoumarin
L-Alanyl-L-alanyl-L-phenylalanine-7-amido-4-methycoumarin TFA
D-Alanyl-L-leucyl-L-lysine-7-amido-4-methylcoumarin
L-Alanyl-L-phenylalanyl-L-lysine-7-amido-4-methylcoumarin salt
L-Arginine-7-amido-4-methylcoumarin-hydrochloride
L-Arginyl-L-arginine-7-amido-4-methylcoumarin trihydrochloride
L-Asparagine-7-amido-4-methylcoumarine TFA
L-Aspartic acid-β-(7-amido-4-methylcoumarin)
N-α-Benzoyl-DL-arginine-7-amido-4-methylcoumarin hydrochloride
N-α-Benzoyl-L-arginine-7-amido-4-methylcoumarin hydrochloride
N-Benzoyl-L-phenylalanyl-L-valyl-L-arginine-7-amido-4-methylcoumarin hydrochloride
N-Benzoyl-L-valyl-glycyl-L-arginine-7-amido-4-methylcoumarin hydrochloride
S-Benzyl-L-cysteine-7-amido-4-methycoumarin
N-BOC-L-Phenylalanyl-L-seryl-L-arginine-7-amido-4-methycoumarin acetate
N-BOC-L-Valyl-glycyl-arginine-7-amido-4-methycoumarin hydrochloride
N-BOC-L-Valyl-Lleucyl-L-lysine-7-amido-4-methycoumarin Salt
N-α-CBZ-L-Arginine-7-amido-4-methycoumarin hydrochloride
N-CBZ-Glycylglycyl-Larginine-7-amido-4-methylcoumarin hydrochloride
N-CBZ-Glycylglycyl-L-leucine-7-amido-4-methycoumarin
N-CBZ-Glycyl-L-proline-7-amido-4-methycoumarin TABLE I-continued N-CBZ-Glycyl-L-prolyl-L-arginine-7-amido-4-methycoumarin hydrochloride
N-β-CBZ-L-lysine-7-amido-4-methycoumarin hydrochloride
N-CBZ-L-Phenylalanyl-L-arginine-7-amido-4-methychloride hydrochloride
N-CBZ-L-Prolyl-L-arginine-7-amido-4-methylcoumarin hydrochloride
L-Citrulline-7-amido-4-methylcoumarin hydrobromide
L-Citrulline-7-amido-4-methylcoumarin TFA
D-Glutamic acid-γ-(7-amido-4-methycoumarin)
L-Glutamic acid-α-(7-amido-4-methycoumarin)
L-Glutamine-7-amido-4-methylcoumarin hydrochloride
Glutaryl-glycyl-L-arginine-7-amido-4-methylcoumarin hydrochloride
Glutaryl-glycylglycyl-L-phenylalanine-7-amido-4-methylcoumarin
Glutaryl-glycylglycyl-L-phenylalanine-7-amido-4-methylcoumarin
Glutaryl-L-phenylalanine-7-amido-4-methycoumarin
Glycine-7-amido-4-methylcoumarin hydrobromide
Glycyl-L-alanine-7-amido-4-methylcoumarin hydrochloride
Glycyl-L-arginine-7-amido-4-methycoumarin salt
Glycylglycine-7-amido-4-methycoumarin hydrochloride
Glycyl-L-phenulalanine-7-amido-4-methycoumarin
Glycyl-L-proline-7-amido-4-methylcoumarin-hydrobomide
L-Histidine-7-amido-4-methylcoumarin
L-Isoleucine-7-amido-4-methycoumarin
L-Isoleucine-7-amido-4-methycoumarin TFA
L-Leucine-7-amido-4-methylcoumarin
L-Leucine-7-amido-4-methylcoumarin hydrochloride
L-Leucyl-L-valvyl-L-tyrosine-7-amido-4-methycoumarin
L-Lysine-7-amido-4-methycoumarin acetate
L-Methionine-7-amido-4-methylcoumarin acetate
N-Methoxysuccinyl-L-alanyl-L-phenylalanyl-L-lysine-7-amido-4-methylcoumarin TFA
N-Methoxysuccinyl-L-aspartyl-L-tyrosol-L-methionine-7-amido-4-methylcoumarin
N-Methoxysuccinylglycyl-L-tryptophyl-L-methionine-7-amido-4-methylcoumarin
L-Ornithine-7-amido-4-methycoumarin carbonate
L-Phenylalanine-7-amido-4-methylcoumarin TFA
L-Proline-7-amido-4-methylcoumarin hydrobomide
L-Prolyl-L-phenylalanyl-L-arginine-7-amido-4-methylcoumarin salt
L-Pyroglutamic acid-7-amido-4-methycoumarin
L-Serine-7-amido-4-methycoumarin hydrochloride
L-Seryl-L-tyrosine-7-amido-4-methycoumarin Hydrate
N-Succinyl-L-alanyl-L-alanyl-L-alanine-7-amido-4-methylcoumarin
N-Succinyl-L-alanyl-L-ananyl-L-henylalanine-7-amido-4-methylcoumarin
N-Succinyl-L-alanyl-L-alanyl-L-valine-7-amido-4-methylcoumarin
N-Succinyl-L-alanyl-L-phenylalanyl-L-lysine-7-amido-4-methylcoumarin
N-Succinyl-L-analyl-L-phenylalanyl-L-lysine-7-amido-4-methylcoumarin TFA
N-Succinyl-L-alanyl-L-prolyl-L-alanine-7-amido-4-methylcoumarin
N-Succinylglycyl-L-proline-7-amido-4-methylcoumarin
N-p-Tosylglycyl-L-proyl-L-arginien-7-amido-4-methycoumarin hydrochloride
N-p-Tosylglycyl-L-prolyl-L-lysine-7-amido-4-methylcoumarin hydrochloride
L-Tyrosine-7-amido-4-methycoumarin

VARIOUS SUBSTRATES

L-Alanine-β-napthylamide
DL-Alanine-β-napthylamide hydrochloride
L-Alanyl-L-alanine-β-naphthylamide
p-Aminobenzyl-1-thio-2-acetamido-2-deoxy-β-D-glucopyranoside
p-Aminobenzyl-1-thio-β-D-galactopyranoside
D-Amygydalin from Apricot Kernels
L-Arginine-4-methozy-β-naphthylamdie hydrochloride
L-Arginine-β-naphthylamide-hydrochloride
N-α-Benzoyl-L-arginine ethylester hydrochloride
N-α-Benzoyl-L-arginine-4-methozy-β-naphthylamide-hydrochloride
N-α-Benzoyl-DL-arginine-β-naphthylamide
N-α-Benzoyl-D-arginine-p-nitroanallide hydrochloride
N-α-Benzoyl-D-arginine-p-nitroanallide hydrochloride
N-α-Benzoyl-D-arginine-p-nitroanalide hydrochloride
6-Benzoyl-2-naphthylphosphate Disodium salt
6-Benzoyl-2-naphthysulfate Potassium salt
Bis(4-nitrophenyl) phosphate Sodium salt
4-Bromomethyl-7-methoxycoumarin
6-Bromo-2-naphthyl acetate
6-Bromo-2-naphthyl-N-acetyl-β-D-glucosaminide
6-Bromo-2-naphthyl-β-D-galactoside
6-Bromo-2-naphthyl-α-D-glucopyranoside
6-Bromo-2-naphthyl-β-D-glucopyranoside
6-Bromo-2-naphthyl-β-D-glucuronide
6-Bromo-2-naphthyl sulfate
6-Bromo-2-naphthyl sulfate Potassium salt
6-Bromo-2-naphthyl-β-D-xylopyranoside
2-Chloro-4-nitrophenyl-N-acetyl-β-D-glucosaminide
2-Chloro-4-nitrophenyl-β-D-cellobioside
2-Chloro-4-nitrophenyl-β-D-xylopryanoside
8-Hydroxyquinoline-β-D-glucuronide
L-Leucine-p-nitroanilide
L-Leucyl-4-methoxy-β-naphthylamide
L-Leucyl-β-naphthylamide
DL-Methionine-β-napthylamide hydrochloride
2-(3'-Methoxyphenyl)-N-acetyl-D-neuraminic acid
Naphthol AS
Naphthol AS-acetate
Naphthol AS-B1-N-acetyl-β-D-glucosaminide
Naphthol AS-β-chloropropionate
Naphthol AS-B1-β-L-fucopyranoside
Naphthol AS-B1-β-D-galactopyranoside
Naphthol AS-B1-β-D-galactosaminide
Naphthol AS-B1-glucopyranoside
Naphthol AS-B1-β-D-glucuronic acid
Naphthol AS-nonanoate
Naphthol AS-γ-phenylbutyrate
Naphthol AS-phenylpropionate
Naphthol AS-phosphate
Naphthol AS-B1-phosphate
Naphthol AS-phosphate Sodium salt
Naphthol AS-B1-phosphate Sodium salt
Naphthol AS-sulphate Potassium salt
Naphthol AS-B1-sulfate Potassium salt
1-Naphthylbutyrate
2-Naphthybutyrate
1-Naphthylcaprylate
2-Naphthylcaprylate
1-Naphthyl-α-D-glactopyranoside
1-Naphthyl-β-D-glactopyranoside
2-Naphthyl-β-D-galactopyranoside
1-Naphthyl-β-D-glucuronide
1-Naphthylphosphate Disodium salt
2-Naphthylphosphate Disodium salt
2-Naphthylphosphate Sodium salt
2-Naphthylphosphate Sodium salt
1-Naphthylphosphate Sodium salt
2-Naphthylsulfate Potassium salt
2-Nitrophenyl-acetate
4-Nitrophenyl-acetate
2-Nitrophenyl-N-acetyl-α-D-galactosaminide
4-Nitrophenyl-N-acetyl-α-D-galactosaminide
4-Nitrophenyl-N-acetyl-β-D-galactosaminide
4-Nitrophenyl-N-acetyl-α-D-glucosaminide
4-Nitrophenyl-N-acetyl-β-D-glucosaminide
4-Nitrophenyl-N-acetyl-1-thio-β-D-glucosaminide
4-Nitrophenyl-α-L-arabinopyranoside
2-Nitrophenyl-butyrate
4-Nitrophenyl-butyrate
4-Nitrophenyl-caprate
4-Nitrophenyl-caproate
3-Nitrophenyl-caprylate
4-Nitrophenyl-caprylate
4-Nitrophenyl-β-D-cellobioside
3-Nitrophenyl-β-D-fucopyranoside
4-Nitrophenyl-α-D-fucopyranoside
4-Nitrophenyl-β-D-fucopyranoside
4-Nitrophenyl-α-L-fucopyranoside
4-Nitrophenyl-β-L-fucopyranoside
2-Nitrophenyl-α-D-galactopyranoside
2-Nitrophenyl-β-D-galactopyranoside
3-Nitrophenyl-α-D-galactopyranoside
3-Nitrophenyl-β-D-galactopyranoside
4-Nitrophenyl-α-D-galactopyranoside
4-Nitrophenyl-β-D-galactopyranoside
2-Nitrophenyl-β-D-galactopyranoside-6-phosphate Cyclohexylammonium salt
4-Nitrophenyl-β-D-galacturonide
4-Nitrophenyl-α-D-glucopyranoside
4-Nitrophenyl-β-D-glucopyranoside
4-Nitrophenyl-β-D-glucuronide

TABLE I-continued

2-Nitrophenyl-β-D-glucuronide
4-Nitrophenyl-glycerol
4-Nitrphenyl-4'-guanidinobenzoate
4-Nitrophenyl-α-D-maltoheptaoside
4-Nitrophenyl-α-D-maltohexaoside
4-Nitrophenyl-α-D-matlopentaoside
4-Nitrophenyl-α-D-maltoside
4-Nitrophenyl-α-D-maltotetraoside
4-Nitrophenyl-α-D-maltotrioside
4-Nitrophenyl-α-D-mannopyranoside
4-Nitrophenyl-β-D-mannopyranoside
2-Nitrophenyl-myristate
4-Nitrophenyl-myristate
2-Nitrophenyl-palmitate
4-Nitrophenyl-palmitate
p-Nitrophenylphosphate Disodium salt Hexahydrate high purity
4-Nitrophenyl-propionate
4-Nitrophenyl-stearate
4-Nitrophenyl-sulfate Potassium salt
2-Nitrophenyl-β-D-thiogalactopyranoside
4-Nitrophenyl-β-D-thiogalactopyranoside
4-Nitrophenyl-β-D-thioglucopyranoside
4-Nitrophenyl-β-D-xylopyranoside
Phenolphthalein diphosphate
Phenolphthalein diphosphate Tetrasodium salt
Phenolphthalein-mono-β-D-galactopyranoside
Phenolphthalein-β-D-glucuronic acid Sodium salt
Phenyl-N-acetyl-α-D-glucosaminide
Phenylethyl-β-D-galactoside
Phenyl-β-D-galactoside
Phenyl-α-D-glucoside
Phenyl-α-D-glucoside tetroacetate
Phenyl-β-D-glucoside tetroacetate
Resorufin-β-D-galactopyranoside
Resorufin-β-D-glucuronide
L-Serine-β-naphthylamide
1-Thio-β-D-galactopyranoside Sodium salt
1-Thio-β-D-glucopyranoside Sodium salt
L-Tyrosine-β-naphthylamide

X-SUBSTRATES (5-Bromo-4-chloro-3-indolyl-Substrates)

5-Bromo-4-chloro-3-indolyl-acetate
5-Bromo-4-chloro-3-indolyl-N-acetyl-β-D-galactosaminide
5-Bromo-4-chloro-3-indolyl-N-aceryl-β-D-glucosaminide
5-Bromo-4-chloro-3-indolyl-butyrate
5-Bromo-4-chIoro-3-indolyl-caprylate
5-Bromo-4-chloro-3-indolyl-Carbohydrates and other Derviates
5-Bromo-4-chloro-3-indolyl-1,3-diacetate
5-Bromo-4-chloro-3-indolyl-β-D-fucopyranoside
5-Bromo-4-chloro-3-indolyl-α-D-galactopyranoside
5-Bromo-4-chloro-3-indoyl-β-D-glucopyranoside
5-Bromo-4-chloro-3-indolyl-β-D-glucuronic acid Cyclohexylammonium salt
5-Bromo-4-chloro-3-indolyl-β-D-glucuronic acid Sodium salt
5-Bromo-4-chloro-3-indolyl-α-D-mannopyranoside
5-Bromo-4-chloro-3-indolyl-phosphate Disodium salt
5-Bromo-4-chloro-3-indoyl-phosphate Potassium salt
5-Bromo-4-chloro-3-indolyl-phosphate p-Toluidine salt
5-Bromo-4-chloro-3-indolyl-sulfate Potassium salt
5-Bromo-4-chlor-3-indolyl-β-D-xylopyranside

Y-SUBSTRATES (Indoxyl-Substrates)

8-Bromomoindoxyl-3-acetate
5-Bromoindoxyl-1,3-diacetate
Indoxyl-1,3-diacetate
Indoxyl-β-D-galactoside
Indoxyl-β-D-glucoside
Indoxyl-β-D-glucuronic acid Cyclohexylammonium salt
3-Indoxyl-phosphate Di(2-amino-2-methyl-1,3-propanediol) salt
3-Indoxyl-phosphate Disodium salt
3-Indoxyl-phosphate p-Toluidine salt
3-Indoxylsulfate Potassium salt

TABLE II

Media Formulation (per liter)

| | (grams) |
|---|---|
| Defined media | 15.36 |
| HEPES (acid) | 4.29 |
| HEPES (Na⁺salt) | 8.38 |
| Bacto Proteose peptone No. 3 (Difco) | 5.00 |
| Potassium nitrate | 5.00 |
| 4-methylumbelliferyl phosphate (Sigma) | 0.025 |
| 4-methylumbelliferyl-β-D-glucoside (Sigma) | 0.025 |
| L-alanine-7-amido-4-methyl coumarin (Sigma) | 0.025 |

TABLE III

Defined Media Composition

| INGREDIENT | CONCENTRATION (mg/L) |
|---|---|
| Ammonium acetate | 500 |
| Magnesium chloride | 95.35 |
| Ferric chloride (6 hydrate) | 2.7 |
| Manganese sulfate (1 hydrate) | 0.273 |
| Potassium chloride | 100 |
| Zinc sulfate (7 hydrate) | 0.8 |
| Calcium chloride (2 hydrate) | 7.38 |
| Sodium chloride | 1000 |
| L-arginine HCl | 1270 |
| L-asparagine (1 hydrate) | 1136 |
| L-aspartic acid | 20 |
| L-cysteine HCl (1 hydrate) | 1450 |
| L-cystine methylester 2 HCl | 340.8 |
| L-glutamic acid | 20 |
| L-glutamine | 2520 |
| Glycine | 500 |
| L-histidine HCl (1 hydrate) | 419 |
| L-Isoleucine | 520 |
| L-leucine | 520 |
| L-lycine HCl | 724.65 |
| L-methionine | 150 |
| L-phenylalanine | 320 |
| L-proline | 1000 |
| L-serine | 30 |
| L-threonine | 480 |
| L-tryptophan | 100 |
| L-tyrosine Na salt (2 hydrate) | 519 |
| L-valine | 460 |
| Adenine | 25 |
| Biotin | 0.5 |
| Choline chloride | 25 |
| Folic acid | 5 |
| I-Inositol | 25 |
| D(+) calcium pantothenate | 25 |
| Nicotinamide | 5 |
| Para aminobenzoic acid | 1 |
| Pyridoxal HCl | 5 |
| Riboflavin | 5 |
| Thiamine HCl | 5 |
| Uracil | 25 |
| Sodium pyruvate | 1000 |

What is claimed is:

1. A method for detecting the presence or measuring the concentration of bacteria in a food product, comprising the steps of:

providing a bacterial growth medium formulated for food testing, which comprises a first enzyme substrate for a phosphatase, a second enzyme substrate for -a glycosidase, and a third enzyme substrate for a peptidase, wherein said first, second and third enzyme substrates cause or produce an identical type of detectable signal when hydrolyzed by their respective enzymes;

inoculating said medium with said food product and incubating said medium under a condition suitable for bacterial growth for a period of time; and detecting or measuring the identical type of detectable signal as an indication of the presence or the concentration of bacteria in said food product;

wherein said first enzyme substrate comprise a substrate for alkaline phosphatase, said second enzyme substrate comprises a substrate for β-D-glucosidase, and said third enzyme substrate comprises a substrate for L-alanine-7-aminopeptidase.

2. The method of claim 1 wherein said first, second and third enzyme substrates each have both a nutrient moiety and a detectable moiety linked together by a covalent bond, and each said enzyme substrate produces a detectable moiety when hydrolyzed, and each said detectable moiety causes or produces said identical type of detectable signal.

3. The method of claim 2, wherein said detectable moiety is a fluorescent moiety and said identical type of detectable signal is a fluorescent signal.

4. The method of claim 1, wherein said first enzyme substrate comprises 4-methylumbelliferyl phosphate, said second enzyme substrate comprises 4-methylumbelliferyl-β-D-glucoside and said third enzyme substrate comprises L-alanine-7-amido-4-methyl coumarin.

5. The method of claim 1, wherein said food product is ground beef.

6. The method of claim 1, wherein said food product is chicken.

7. The method of claim 1, wherein said food product is drinking water.

8. The method of claim 1, wherein said period of time is no more than 48 hours.

9. A method for detecting the presence or measuring the concentration of bacteria in a food product, comprising the steps of:

providing a bacterial growth medium formulated for food testing, which comprises a first enzyme substrate for a phosphatase, a second enzyme substrate for a glycosidase, and a third enzyme substrate for a peptidase, wherein said first, second and third enzyme substrates cause or produce an identical type of detectable signal when hydrolyzed by their respective enzymes;

inoculating said medium with said food product and incubating said medium under a condition suitable for bacterial growth for a period of time; and detecting or measuring the identical type of detectable signal as an indication of the presence or the concentration of bacteria in said food product;

wherein said first enzyme substrate is selected from the group consisting of: a substrate for alkaline phosphatase, a substrate for acid phosphatase, and a substrate for pyrophosphatase; and said second enzyme substrate is selected from the group consisting of: a substrate for N-acetyl-β-D-galactosaminidase, a substrate for N-acetyl-β-D-glucosaminidase, a substrate for neuraminidase, a substrate for L-arabinopyranosidase, a substrate for β-D-fucosidase, a substrate for α-D-galactosidase, a substrate for β-D-galactosidase, a substrate for α-D-glucosidase, a substrate for β-D-glucosidase, a substrate for β-D-glucuronidase, a substrate for α-D-mannosidase, a substrate for β-D-xylosidase; and said third enzyme substrate is selected from the group consisting of: a substrate for peptidase, a substrate for (L or D amino acid)-aminopeptidase, a substrate for L-alanine aminopeptidase, a substrate for trypsin, and a substrate for chymotrypsin.

10. A bacterial growth medium formulated for food testing, comprising a first enzyme substrate for a phosphatase, a second enzyme substrate for a glycosidase, and a third enzyme substrate for a peptidase, wherein said first, second and third enzyme substrates cause or produce an identical type of detectable signal when hydrolyzed by their respective enzymes;

wherein said first enzyme substrate comprises a substrate for alkaline phosphatase, said second enzyme substrate comprises a substrate for β-D-glucosidase and said third enzyme substrate comprises a substrate for L-alanine-aminopeptidase.

11. The medium of claim 10, wherein said first, second and third enzyme substrates each have both a nutrient moiety and a detectable moiety linked together by a covalent bond, and each said enzyme substrate produces a detectable moiety when hydrolysed, and each said detectable moiety causes or produces said identical type of detectable signal.

12. The method of claim 11, wherein said detectable moiety is a fluorescent moiety and said identical type of detectable signal is a fluorescent signal.

13. The medium of claim 10, wherein said first enzyme substrate comprises 4-methylumbelliferyl phosphate, said second enzyme substrate comprises 4-methylumbelliferyl-β-D-glucoside and said third enzyme substrate comprises L-alanine-7-amido-4-methyl coumarin.

14. The medium of claim 10, wherein said food product is ground beef.

15. The medium of claim 10, wherein said food product is chicken.

16. The medium of claim 10, wherein said water sample is drinking water.

17. The medium of claim 10, wherein said medium is a liquid.

* * * * *